(12) United States Patent
Camus

(10) Patent No.: US 8,041,411 B2
(45) Date of Patent: *Oct. 18, 2011

(54) DEVICE AND METHOD FOR CONTROLLING A MAGNETIC ELEMENT IN THE BODY OF A PATIENT

(75) Inventor: Estelle Camus, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 1080 days.

This patent is subject to a terminal disclaimer.

(21) Appl. No.: 11/455,246

(22) Filed: Jun. 16, 2006

(65) Prior Publication Data

US 2007/0016013 A1   Jan. 18, 2007

(30) Foreign Application Priority Data

Jun. 17, 2005 (DE) .......................... 10 2005 028 226

(51) Int. Cl.
*A61B 5/00* (2006.01)
(52) U.S. Cl. ........................................ 600/424; 606/130
(58) Field of Classification Search .................. 600/424; 606/130
See application file for complete search history.

(56) References Cited

U.S. PATENT DOCUMENTS

| 6,212,419 | B1 | 4/2001 | Blume et al. | |
|---|---|---|---|---|
| 7,280,863 | B2* | 10/2007 | Shachar | 600/424 |
| 2004/0034283 | A1* | 2/2004 | Quaid, III | 600/300 |
| 2005/0197566 | A1* | 9/2005 | Strommer et al. | 600/424 |
| 2005/0203382 | A1* | 9/2005 | Govari et al. | 600/424 |
| 2006/0287824 | A1* | 12/2006 | Lin | 701/214 |
| 2008/0249395 | A1* | 10/2008 | Shachar et al. | 600/409 |
| 2010/0130854 | A1* | 5/2010 | Shachar et al. | 600/424 |

FOREIGN PATENT DOCUMENTS

WO   WO 2004/006795 A1   1/2004

* cited by examiner

*Primary Examiner* — Brian Casler
*Assistant Examiner* — Amanda Lauritzen

(57) ABSTRACT

A device for the magnet-assisted catheter intervention comprises magnets for controlling a magnetic tip of a catheter. An x-ray device serves to generate three dimensional ambient images of a patient. A data processing unit calculates the probability of the magnetic tip colliding with an obstacle in the body of the patient from the ambient images and the current position of the magnetic tip and if necessary acts mechanically on the guide element so as to generate a haptically perceivable signal, with which guide element the movement of the catheter is controlled.

13 Claims, 3 Drawing Sheets

DEVICE AND METHOD FOR CONTROLLING A MAGNETIC ELEMENT IN THE BODY OF A PATIENT

CROSS REFERENCE TO RELATED APPLICATIONS

This application claims priority of German application No. 10 2005 028 226.1 filed Jun. 17, 2005, which is incorporated by reference herein in its entirety.

The invention relates to a device for controlling a magnetic element in the body of a patient, comprising:
- a magnetic field generator, the magnetic field of which guides the magnetic element within the body of the patient,
- a navigation device, which generates location information about the position of the magnetic element in the body of the patient, and
- a guide device connected to the magnetic field generator and which can be operated by a user, which comprises a guide element which can be operated by a user by means of force effect.

FIELD OF THE INVENTION

A device of this type is known from U.S. Pat. No. 6,212,419 B1. The known device is able to navigate a magnetic element in the body of a patient with the aid of one or a number of magnets in the body of a patient. To this end, markers are fixed to the magnets or the support thereof, the position of which can be detected by position sensors fixed to a support. Furthermore, markers are also fixed to the body of the patient, the position of which can be detected by the position sensors. The markers applied to the body of the patient are provided such that they can also be detected in a computed tomography device by an x-ray device or a magnetic resonance device. Display devices are provided in order to enable the user to control the magnetic element in the body of the patient, on which display devices the current magnetic field generated by the magnet or magnets superimposes an image of the body of the patient. The image of the body of the patient can be recorded here with the aid of an x-ray device, a computed tomography device or a magnetic resonance device. The images are registered here with the aid of the markers fixed to the magnet/s as well as to the body of the patient.

The magnetic element used with the known device is generally the tip of a catheter, which is guided through vessels or other body cavities with the aid of the external magnetic field. One advantage of this device is that the tip of the catheter can also be guided into body cavities which can otherwise not be reached. The catheter is frequently not moved manually, but is instead moved with the aid of a control device, which moves the catheter in a controlled manner from a computer.

In this case, the treating doctor has no control over whether the tip of the catheter strikes an obstacle in the body of the patient. An obstacle of this type may be a vascular wall for instance. Since the treating doctor does not move the catheter himself, he/she does not notice the counteracting force developing when the catheter tip collides with an obstacle. In the best case scenario, the doctor can recognize that the tip of the catheter has struck an obstacle by the behavior of the catheter or the catheter tip in an x-ray image. If the catheter tip rolls up for instance, this means that the catheter tip is touching an obstacle and can thus not be guided further in the direction predetermined by the magnetic field.

Even when feeding the catheter manually, collisions are to be avoided as far as possible in order to protect the tissue.

BACKGROUND OF THE INVENTION

Starting from this prior art, the object underlying the invention is thus to create a device for controlling a magnetic element in the body of a patient, which prevents collisions in the body of the patient as far as possible.

This object is achieved by a device with the features of the independent claims. Advantageous embodiments and developments are specified in the dependent claims.

The device is characterized in that a monitoring device monitors the position of the magnetic element in the body of the patient on the basis of location information supplied by the navigation device. The monitoring device applies a control device with control signals, which act mechanically on the guide element when the magnetic element approaches an obstacle in order to generate a haptically perceivable signal.

The mechanical effect on the guide element indicates to the user that a collision is imminent. The user is then able to change the desired movement direction of the magnetic element so as to prevent the magnetic element from colliding with the surrounding tissue. The particular advantage of the signal which can be haptically perceived at the guide element is that the signal is directly communicated in conjunction with a guide process. If a guide process is carried out by a user and the user reaches for the guide element, a warning signal is directly transmitted to the user's hand. Thus the user need not first associate the significance of optically or acoustically communicated warning signals with the danger of collision, but the significance of the haptical warning signal is instead intuitively clear to the user.

With a preferred embodiment, the control device is an inhibitor, which counteracts the force effect of the user on the guide element when the magnetic element approaches an obstacle.

The inhibitor counteracting the force effect of the user on the guide element allows a counteracting force to be communicated to the user when the magnetic element approaches the obstacle, said counteracting force indicating to the user that the magnetic element is located in the vicinity of an obstacle. Misdirections are hereby effectively avoided.

The inhibitor preferably exerts a force on the guide element, which is increases as the distance between the magnetic element and the obstacle diminishes. The extent of the danger of collision or the severity of the collision is hereby communicated intuitively to the user.

The navigation device has a position image generator in order to determine the necessary location information, said position image generator determining a current position image of the magnetic element in the body of the patient. In this way, the position image generator can evaluate current x-ray images from an x-ray device or current ultrasound images from an ultrasound device. Furthermore, the navigation device has an ambient image generator, which advantageously generates current ambient information about the ambient of the magnetic element. In this way, the ambient image generator can evaluate image information supplied by an x-ray device, an ultrasound device or by a magnetic resonance device depending on the application case.

Furthermore, it is possible for the ambient image generator to refer back to the ambient information stored in a data base.

The navigation device finally features a position analyzer, which relates the current position of the magnetic element to the ambient information. The monitoring device is then able to determine on the basis of the location information supplied by the position analyzer whether a movement of the magnetic element desired by the user by actuating the guide element results in its coming into proximity with an obstacle and if necessary, to apply the inhibitor with suitable control signals in order to inhibit the movement of the guide element.

To register the position image and the ambient image, the position analyzer advantageously refers back to markers which are fixed to the body of the patient or to the magnetic element.

Advantageously, the magnetic element can be the tip of a catheter or a part of an endorobot or the entire endorobot.

BRIEF DESCRIPTION OF THE DRAWINGS

Further advantages and details of the invention emerge from the description below, in which exemplary embodiments of the invention are described in detail with reference to the drawings, in which.

DETAILED DESCRIPTION OF THE INVENTION

Figure 1:
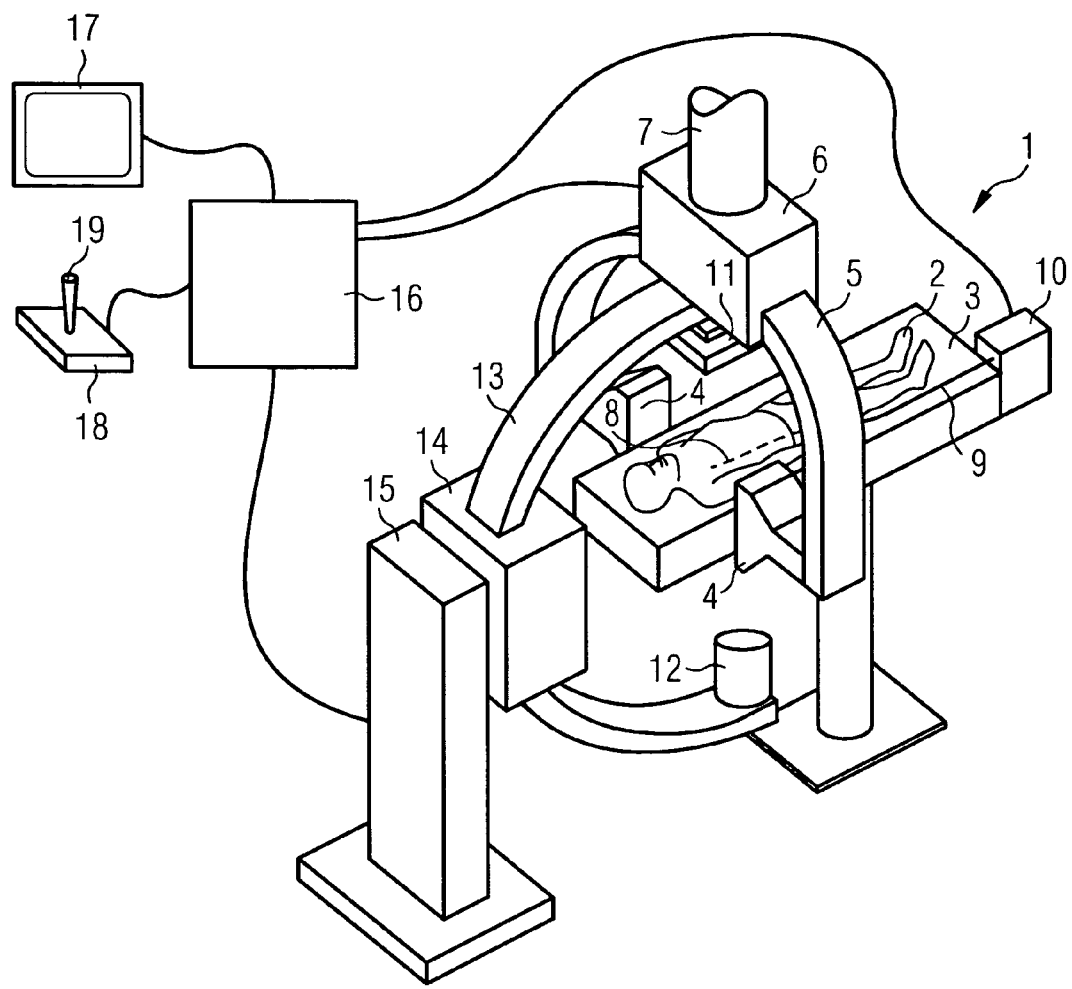
FIG. 1 shows a perspective view of a device for the magnetic control of a magnetic element in the body of a patient.

FIG. 1 shows a perspective view of a device 1 for the magnetic field-assisted treatment of a patient 2. During the treatment, the patient 2 lies on a patient support 3 in a magnetic field generated by magnets 4. The magnets 4 can be both permanent magnets and also electromagnets. With the device illustrated in FIG. 1, the magnets 4 are fixed to a curved magnet arm 5, which is mounted on a magnet arm support 6 and moveable in the circumferential direction. The magnet arm support 6 is fixed to the ceiling on a pivoting mounting via magnet arm support 7. Furthermore, the magnets 4 are also fixed to the magnet arm 5 in a moveable manner. The movement of the magnets 4 allows the orientation and the strength of the magnetic field in the body of the patient 2 to be influenced. This allows a magnetic tip 8 of a catheter 9 or endorobot to be controlled. The catheter 9 or endorobot can also be withdrawn from the magnetic field generated by the magnets 4. In addition, a catheter drive 10 can also be provided, which allows the catheter 9 to be fed into a vessel of the patient 2.

An x-ray detector 11 is provided to monitor the movement of the catheter 9 in the body of the patient 2, said x-ray detector being supplied with radiation from an x-ray source 12. The x-ray detector 11 and the x-ray source 12 are fixed to an x-ray arm 13, which is mounted on an x-ray arm support 14 and is moveable in the circumferential direction. The x-ray arm support 14 is fixed to an x-ray arm support 15 in a pivotable fashion.

It should be noted that further x-ray devices or ultrasound devices can be provided, with which the movement of the catheter 9 in the body of the patient 2 can be monitored. These x-ray devices do not necessarily need to be fixed to an x-ray arm 13. In fact different types of supports are conceivable. Also, the magnets 4 must not necessarily be fixed to the magnet arm 5. In fact, the magnets 4 can also be fixed to a support set up on the floor.

A data processing unit 16 is provided to control the device 1, which is connected inter alia to a monitor 17 and a control device 18. The control device 18 particularly comprises a control joystick 19, which can be operated by the user manually in order to guide the catheter 9 in the body of the patient 2 in a desired direction, and if necessary to control the feed.

The x-ray detector 11 and the x-ray source 12, as well as the control facilities required for the method of the x-ray arm 13 are additionally connected to the data processing unit. Furthermore, a connection exists with the control facilities required for moving the magnets 4 and the magnet arm 5, as well as with the catheter drive 10.

Figure 2:
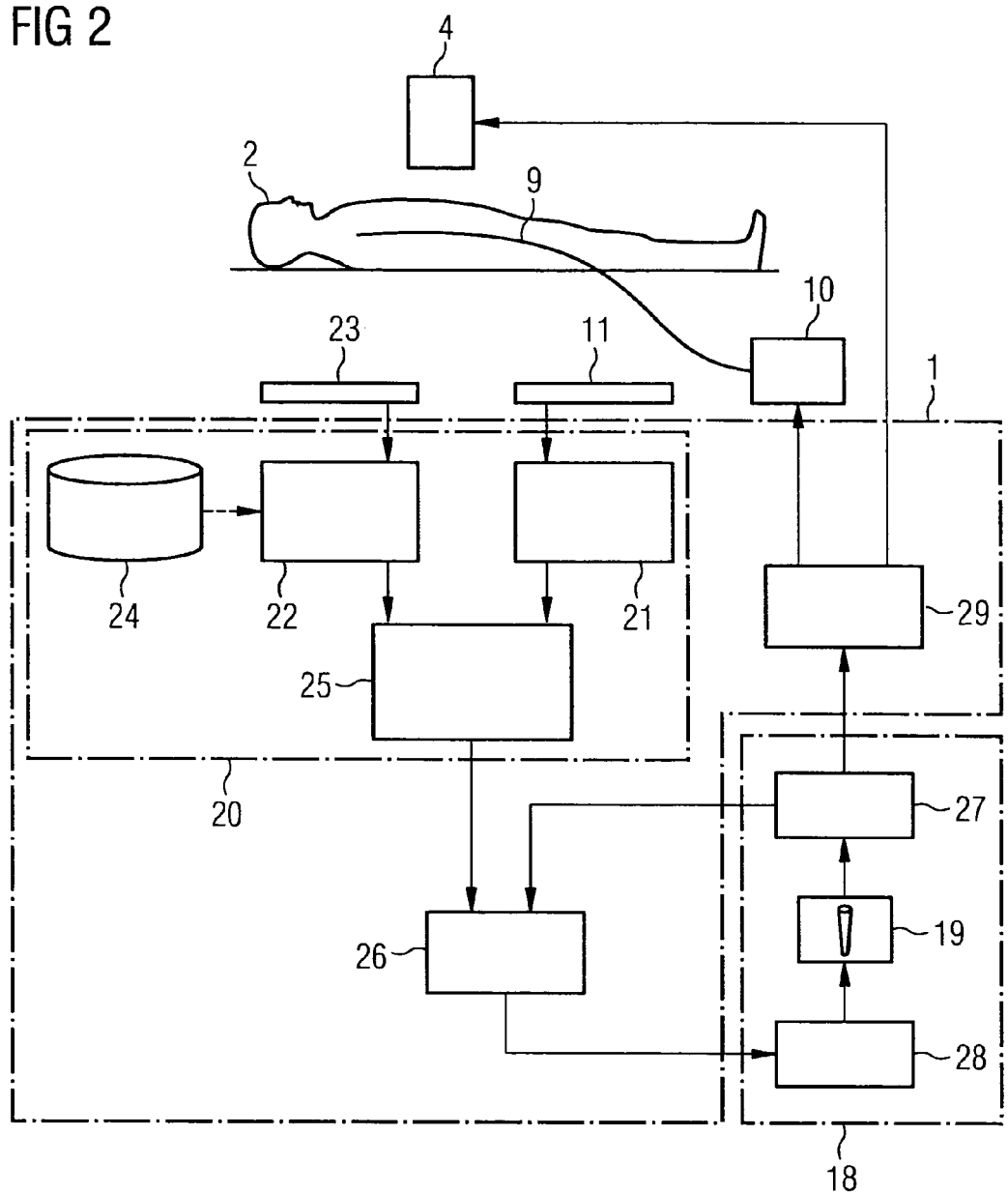
FIG. 2 shows a block diagram of the device for controlling the magnetic element in the body of the patient.

FIG. 2 shows a block diagram, in which different function units of the data processing unit 16 are displayed. The data processing unit 16 in particular has a navigation device 20 comprising a position image generator 21, which is connected to the x-ray detector 11. The position image generator 21 generates a current image of the respective position of the catheter 9 in the body of the patient 2. Position information relating to the position of the catheter 9 in the body of the patient 2 is generated on the basis of the current image of the position of the catheter 9 in the body of the patient 2.

The navigation device 20 further comprises an ambient image generator 22, which is connected to a detector 23. The detector 23 can be identical to the x-ray detector 11 or an image acquisition system independent of x-ray detector 11, so that the device 1 shown in FIG. 1 is supplemented. This image acquisition system can operate with ultrasound, x-rays or other imaging methods. From the data supplied by the detector 23, the ambient image generator 22 generates an image of the environment, in which the magnetic tip 8 of the catheter 9 or endorobot is currently located. In this way, the ambient image generator 22 can refer back to ambient information stored in a data base 24. A registering device 25 arranged downstream of the position image generator 21 and the ambient image generator 22 makes the position image generated by the position image generator 21 and the ambient image generated by the ambient image generator 22 coincide. Here, the registering device 24 advantageously uses markers, which can be recognized both in the position image as well as in the ambient image.

The data output by the navigation device 20, in particular the registering device 25, is fed to a monitoring device 26. The monitoring device 26 is further fed with data from a control joystick sensor 27, which detects the movement of the control joystick 19. The monitoring device 26 checks whether the movement predetermined by the user by actuating the control joystick 19 results in a collision with an obstacle. If a collision with an obstacle can occur, the monitoring device 26 feeds an inhibitor 28 with control signals, by means of which the movement of the control joystick 19 is inhibited. The user actuating the control joystick 19 then perceives a counteracting force, which is stronger, the smaller the distance between the magnetic tip 8 of the catheter 9 or endorobot and the obstacle in the body of the patient 2. A haptical or tactile message relating to the interaction of the magnetic tip 8 with the tissue of the patient 2 is hereby communicated to the user.

The control joystick sensor 27 finally also feeds a drive controller 29 with control signals. The drive controller 29 prompts the catheter 9 to be moved according to the movement of the control joystick 19 with the aid of magnets 4 and the catheter drive.

It should be noted that the position image generator 21, the ambient image generator 22 and the registering device 25 are functional units. These functional units are not necessarily linked to specific physical components, but instead can be distributed over a number of physical units. The components can also be realized with the aid of software.

Figure 3:
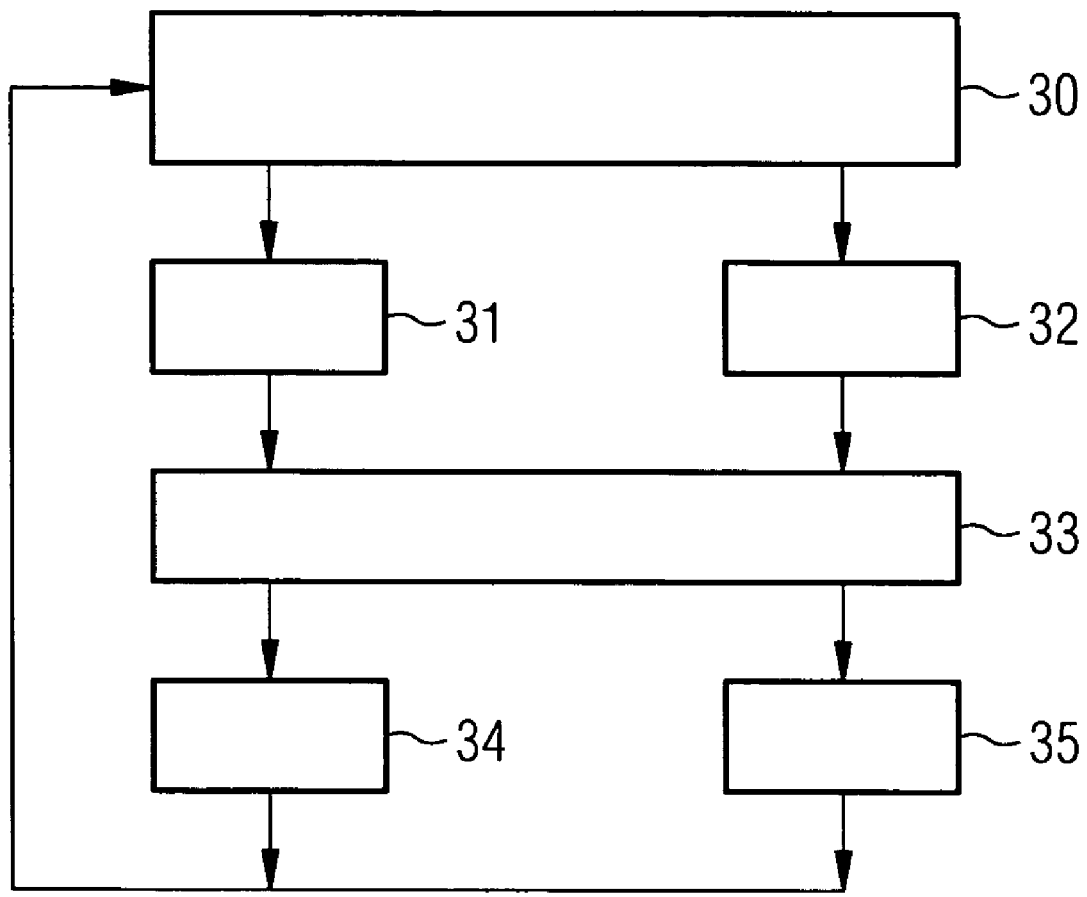
FIG. 3 shows a flow diagram of the method implemented by the device for controlling the magnetic element.

A flow diagram is illustrated in FIG. 3 to clarify the monitoring process, which shows the method steps implemented by the data processing unit 16. An x-ray image recording 30 is first carried out with the aid of the x-ray source 12 and the x-ray detector 11. The x-ray images generated during the x-ray image recording 30 can be immediately used to visualize the position of the catheter 9 on the monitor 17. The vectors are determined by means of a subsequent read-out process, said vectors specifying the movement of the magnetic tip 8 of the catheter 9 or endorobots in the desired direction. During the read-out process 31, the positioning of the control joystick 19 is read out for instance by the monitoring device 16.

In parallel with the read-out process 31, an image processing 32 is carried out on the basis of x-ray images generated by the x-ray image recording 30, by means of which image processing 32, a three-dimensional image data set is generated, which describes the tissue of the patient 2 surrounding the catheter 9. A comparison process 33 is finally carried out, in which it is monitored on the basis of the three-dimensional data set generated in the image processing 32, whether the desired movement of the catheter 9 determined in the read-out process results in a collision. Both the collision risk and also the intensity of the collision can be quantified in this way. The external magnetic fields are then adjusted in a control process 34 by means of a suitable movement of the magnets 4 such that the magnetic tip 8 of the catheter 9 or endorobot moves in the desired direction. At the same time, the catheter 9 or endorobot can be moved with the aid of the catheter drive 10. A manual operation of the catheter 9 or endorobot is also conceivable.

If the comparison process 33 indicates the collision of the magnetic tip 8 with an obstacle, an inhibition process 35 is triggered, by means of which the movement of the control device 18 is inhibited. An acoustic signal which indicates a collision can also be output if necessary. Furthermore, it is possible to notify the user of the risk of a collision by means of a corresponding color selection when displaying the current position image on the monitor 17.

The image processing 32, by means of which three-dimensional ambient images of the catheter 9 are generated, can be carried out on the basis of different image information. It is possible for instance, to use ultrasound data to generate the three-dimensional ambient images. To this end, two-dimensional ultrasound images are first recorded in real-time during the catheter intervention. The two-dimensional ultrasound images can either be recorded extracorporeally with a conventional ultrasound head or intracorporeally with an ultrasound catheter positioned within the body of the patient 2. This ultrasound catheter can be a separate catheter, which is fed into an adjacent vessel. Furthermore, it is possible to provide the catheter 9 or endorobot provided with the magnetic tip 8 with an ultrasound head. The three-dimensional ultrasound images are then generated from the two-dimensional ultrasound images by a three-dimensional reconstruction. The three-dimensional ultrasound images can be generated at any time throughout the catheter intervention. The three-dimensional ultrasound images can thus be regenerated after changing the anatomical ratios during the catheter interventions. The three-dimensional ultrasound images are generated in this case almost in real-time. It is further possible to generate three-dimensional images in real-time during the intervention with a plurality of conventional ultrasound heads.

It is further possible to record two-dimensional cross-sectional images of the body of the patient prior to the catheter interventions with the aid of a computed tomography device or a magnetic resonance device, and to generate three-dimensional volume images in advance by means of a three-dimensional reconstruction from these cross-sectional images. The tissue can however take the form of moveable body tissue. This is the case for instance with body tissues in the region of the heart. The cross-sectional images recorded prior to the catheter intervention with the aid of a computed tomography device or a magnetic resonance device thus generally only display the body tissue at a specific time. In this case, a model dependent on the temporally variable parameters for the deformation of the body tissue is created in order to be able to reconstruct the missing ambient images. Breathing or heart phase parameters can also serve as parameters for this model.

It is finally possible to generate three-dimensional ambient images from the x-ray projection images recorded from different angles during the catheter intervention with the aid of the x-ray detector 11 and the x-ray source 12. These three-dimensional ambient images can be regenerated during the catheter intervention after changing the anatomical conditions, so that current imaging images are available almost in real-time.

The current two-dimensional position images and the three-dimensional ambient images can be registered using conventional position acquisition system based on optical or electromagnetic sensors, or using anatomical markers. When the three-dimensional ambient image is generated with the aid of ultrasound, markers on the ultrasound head or anatomical markers can be used. When the three-dimensional ambient image is based on data which has been generated with the aid of a computed tomography device or a magnet resonance device, anatomical markers can be used. When the three-dimensional ambient images are finally generated with the aid of the x-ray detector 11 and the x-ray source 12, the registering can be used, which assigns the position of the magnets 4 and the position of the magnetic tip 8 of the catheter 9 or endorobot to the x-ray images generated with the aid of the x-ray source 12 and the x-ray detector 11.

By means of the device described here, the user and in particular the treating doctor receives a haptical message about the movement of the catheter 9 in the body of the patient 2. The catheter interventions are hereby more reliable in angiography and heart catheter labs. Furthermore, the guidance of the catheter 9 by the treating doctor is simplified. Furthermore, the movement of the catheter 9 can also be implemented more quickly, since the treating doctor is immediately informed of a possible collision by the device 1. The treating doctor can hereby immediately correct or at least finely adjust the guidance of the catheter by readjusting the desired movement.

It should be noted that a haptically perceivable warning signal can be communicated to the user by vibrating or oscillating the control joystick 19. The amplitude of the oscillation is hereby preferably greater, the greater the collision risk or the severity of the collision.

It is further worth noting that aside from the control joystick 19, further control elements which can be operated by force effect can be considered for the control of the magnetic tip 8. By way of example, pedals, steering wheels, tracker balls or other similar devices which can be operated with the feet can also be used.

The invention claimed is:

1. A device for controlling a magnetic element in a body of a patient, comprising:
    (a) a magnetic field generator for generating a magnetic field which guides the magnetic element in the body of the patient;
    (b) a navigation device for generating a location information about a position of the magnetic element in the body of the patient wherein the location information comprises real-time three-dimensional information and information about tissue near the magnetic element in the body of the patient, wherein the navigation device further comprises a position image generator configured to evaluate a current x-ray image, magnetic resonance image, and/or ultrasound image where the magnetic element is located within the body and an ambient image generator configured to generate ambient information about an ambient environment of the magnetic element, so that image information can be evaluated against the ambient information and/or a current position of the magnetic element can be related to the ambient information with a position analyzer;

(c) a monitoring device for monitoring the position of the magnetic element in the body of the patient based on the location information supplied by the navigation device; a guide device connected to the magnetic field generator comprising a guide element which is manually operable by a force effect of a user;

(d) a control device fed with a control signal by the monitoring device and mechanically acting on the guide element when the magnetic element approaches an obstacle to generate a haptically perceivable signal communicated to a user tactically, visually; and/or acoustically to warn the user of the obstacle in advance of a collision; and (e) an inhibitor which counteracts the force effect of the user on the guide element when the magnetic element approaches the obstacle and configured such that the force exerted on the guide element by the inhibitor increases as a distance between the magnetic element and the obstacle diminishes.

2. The device as claimed in claim 1, wherein the ambient image generator refers back to ambient image data stored in a database to create the three-dimensional ambient image to include a model dependent on a temporally variable parameters for a deformation of a body tissue.

3. The device as claimed in claim 1, wherein the monitoring device is fed with a movement data describing a movement of the magnetic element.

4. The device as claimed in claim 1, wherein a sensor device of the guide element generates a control data which displays a movement of the magnetic element and feed the control data to the monitoring device.

5. The device as claimed in claim 1, wherein the magnetic element is a tip of a catheter.

6. The device as claimed in claim 1, wherein the magnetic element is a part of an endorobot.

7. The device as claimed in claim 1, wherein the guide element is selected from the group consisting of: a control joystick, a pedal, a steering wheel, and a tracker ball.

8. The device as claimed in claim 1, wherein the haptically perceivable signal is directly communicated with a guide process.

9. The device as claimed in claim 1, further comprises a position analyzer and at least one marker fixed to the body of the patient and/or the magnetic element, configured to register a position image and ambient image of the magnetic element.

10. The device as claimed in claim 1, further comprising:
a registering device which registers a position image generated by a position image generator in the ambient images and assists with a registering marker which is recognized both in the position image and the ambient image.

11. A method for controlling a magnetic element in a body of a patient, comprising:
(a) generating a magnetic field by a magnetic field generator which guides the magnetic element in the body of the patient;
(b) providing a location information about a position of the magnetic element in the body of the patient by a navigation device wherein the location information comprises real-time three-dimensional information and information about tissue near the magnetic element in the body of the patient by evaluating a current x-ray image, magnetic resonance image, and/or ultrasound image, with a position image generator, where the magnetic element is located within the body;
(c) determining ambient information about an ambient environment of the magnetic element, with an ambient image generator, so that image information can be evaluated against the ambient information and/or a current location of the magnetic element can be related to the ambient information with a position analyzer;
(d) monitoring the position of the magnetic element in the body of the patient by a monitoring device based on the location information supplied by the navigation device;
(e) manually operating a guide element by a force effect of a user; feeding a control signal to an inhibitor control device from the monitoring device; mechanically acting on the guide element by the inhibitor control device when the magnetic element approaches an obstacle to generate a tactilely perceivable signal to warn the user of the obstacle in advance of a collision;
(f) communicating the tactilely perceivable signal to a user tactically, visually, and/or acoustically; and
(g) counteracting the force effect of the user on the guide element with the inhibitor control device when the magnetic element approaches the obstacle such that the force increases as a distance between the magnetic element and the obstacle diminishes.

12. The device as claimed in claim 11, further comprises registering a position image and an ambient image with a position analyzer which uses at least one marker fixed to the body of the patient and/or to the magnetic element.

13. The method as claimed in claim 11, further comprising:
registering a position image generated by a position image generator in the ambient images and assists with a registering marker which is recognized both in the position image and in the ambient image.

* * * * *